(12) United States Patent
Butler et al.

(10) Patent No.: US 10,046,118 B2
(45) Date of Patent: Aug. 14, 2018

(54) BEARING FOR A PISTON ROD BODY FOR A DRUG DELIVERY DEVICE, A PISTON ROD ARRANGEMENT AND A PISTON ROD BODY

(71) Applicant: Sanofi-Aventis Deutschland GmbH, Frankfurt am Main (DE)

(72) Inventors: Stephen David Butler, Staffordshire (GB); Mark Philip Horlock, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 63 days.

(21) Appl. No.: 14/402,299

(22) PCT Filed: May 28, 2013

(86) PCT No.: PCT/EP2013/060912
§ 371 (c)(1),
(2) Date: Nov. 19, 2014

(87) PCT Pub. No.: WO2013/178600
PCT Pub. Date: Dec. 5, 2013

(65) Prior Publication Data
US 2015/0133874 A1    May 14, 2015

(30) Foreign Application Priority Data
May 30, 2012    (EP) .................................... 12170069

(51) Int. Cl.
*A61M 5/315*    (2006.01)

(52) U.S. Cl.
CPC .... *A61M 5/31511* (2013.01); *A61M 5/31515* (2013.01)

(58) Field of Classification Search
CPC ...................... A61M 5/31511; A61M 5/31515
(Continued)

(56) References Cited

U.S. PATENT DOCUMENTS

| 533,575 | A | 2/1895 | Wilkens |
|---|---|---|---|
| 4,677,980 | A | 7/1987 | Reilly et al. |

(Continued)

FOREIGN PATENT DOCUMENTS

| CA | 2138528 | 12/1998 |
|---|---|---|
| CA | 2359375 A1 | 7/2000 |

(Continued)

OTHER PUBLICATIONS

English Translation of First Office Action issued in Chinese Patent Application No. 201380026655.X dated Jul. 26, 2016.
(Continued)

*Primary Examiner* — Deanna K Hall
(74) *Attorney, Agent, or Firm* — Fish & Richardson P.C.

(57) ABSTRACT

The present disclosure concerns a bearing for a piston rod body for a drug delivery device. The bearing has an axis and comprises a first and a second surface which are spaced apart in the direction of the axis and a third surface, wherein the third surface connects the first and the second surface, wherein an opening is provided in each of the first and the third surface, and wherein the opening in the first surface is connected to the opening in the third surface. Further, the present disclosure concerns a piston rod body and a piston rod arrangement comprising said bearing and the piston rod body.

15 Claims, 8 Drawing Sheets

(58) Field of Classification Search
USPC .......................................................... 604/223
See application file for complete search history.

(56) References Cited

U.S. PATENT DOCUMENTS

| | | | |
|---|---|---|---|
| 4,865,591 A | 9/1989 | Sams | |
| 4,911,965 A | 3/1990 | Lindner | |
| 5,007,904 A * | 4/1991 | Densmore | A61M 5/007 600/432 |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,780,387 A | 7/1998 | Harada | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,390,313 B2 | 6/2008 | Bonacci | |
| 7,678,084 B2 | 3/2010 | Judson et al. | |
| 7,850,662 B2 | 12/2010 | Veasey et al. | |
| 8,038,656 B2 * | 10/2011 | Lloyd | A61M 5/31515 604/218 |
| 8,186,233 B2 | 5/2012 | Joung et al. | |
| 8,304,152 B2 | 11/2012 | Wu | |
| 8,961,020 B2 | 2/2015 | Holdgate et al. | |
| 9,089,656 B2 | 7/2015 | Plumptre | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0184103 A1 | 8/2006 | Paproski et al. | |
| 2007/0016143 A1 | 1/2007 | Miller et al. | |
| 2008/0082055 A1 | 4/2008 | Lloyd et al. | |
| 2009/0275916 A1 | 11/2009 | Harms et al. | |
| 2012/0095413 A1 | 4/2012 | Nzike et al. | |

FOREIGN PATENT DOCUMENTS

| | | |
|---|---|---|
| CN | 1744925 A | 3/2006 |
| CN | 102458527 A | 5/2012 |
| CN | 102470208 A1 | 5/2012 |
| EP | 0496141 A1 | 7/1992 |
| EP | 0897729 A2 | 2/1999 |
| EP | 0937471 A2 | 8/1999 |
| EP | 0937476 A2 | 8/1999 |
| EP | 1776975 A2 | 4/2007 |
| EP | 2438951 A1 | 4/2012 |
| FR | 2850283 A1 | 7/2004 |
| WO | 9307922 A1 | 4/1993 |
| WO | 9324160 A1 | 12/1993 |
| WO | 9938554 A1 | 8/1999 |
| WO | 0110484 A1 | 2/2001 |
| WO | 0134089 A1 | 5/2001 |
| WO | 0207812 A2 | 1/2002 |
| WO | 0230495 A2 | 4/2002 |
| WO | 02092153 A2 | 11/2002 |
| WO | 03080160 A1 | 10/2003 |
| WO | 2006084876 A1 | 8/2006 |
| WO | 2011154481 A1 | 12/2011 |
| WO | 2011154482 A2 | 12/2011 |
| WO | 2011154486 A1 | 12/2011 |
| WO | 2011154490 A1 | 12/2011 |

OTHER PUBLICATIONS

English Translation of Notification of Reason(s) for Rejection issued in Japanese Patent Application No. 2015-514454 dated Apr. 25, 2017.

* cited by examiner

BEARING FOR A PISTON ROD BODY FOR A DRUG DELIVERY DEVICE, A PISTON ROD ARRANGEMENT AND A PISTON ROD BODY

CROSS REFERENCE TO RELATED APPLICATIONS

The present application is a U.S. National Phase Application pursuant to 35 U.S.C. § 371 of International Application No. PCT/EP2013/060912 filed May 28, 2013, which claims priority to European Patent Application No. 12170069.4 filed May 30, 2012. The entire disclosure contents of these applications are herewith incorporated by reference into the present application.

FIELD OF INVENTION

The present disclosure relates to a bearing for a piston rod body for a drug delivery device, to a piston rod arrangement and to a piston rod body.

BACKGROUND

Further, a drug delivery device comprising a piston rod is disclosed. The drug delivery device may be e.g. a pen-type injector.

It is an object to provide for a bearing which facilitates an improved assembly to a piston rod body. It is another object to provide for a piston rod arrangement which facilitates improved assembly of the bearing to a piston rod body. Furthermore, a novel, in particular an improved piston rod body should be provided.

This object may be achieved by a bearing for a piston rod arrangement for a drug delivery device, by a piston rod arrangement and by a piston rod body according to the independent claims. Further features, advantageous embodiments and expediencies are subject-matters of the dependent claims.

SUMMARY

According to one aspect, a bearing for a piston rod body for a drug delivery device has an axis, the bearing comprising a first and a second surface which are spaced apart in the direction of the axis, and a third surface, wherein the third surface connects the first and the second surface. An opening may be provided in each of the first and the third surface. The opening in the first surface may be connected to the opening in the third surface.

The first surface of the bearing may be formed by a fixing proximal end wall. In particular, the fixing proximal end wall may fix the bearing to a piston rod body. The second surface of the bearing may be formed by a bung contact wall or a distal end wall. The bearing may be used in a drug delivery device. The bearing may be adapted to be assembled with a piston rod body to form a piston rod for a drug delivery device. In particular, in the drug delivery device the bung contact wall of the bearing may be in direct contact to a bung, e.g. a bung arranged within a cartridge which contains the drug to be dispensed from the device. In particular, the distal end wall of the bearing may be arranged to abut a proximal end face of the bung. The third surface of the bearing may be formed by a sidewall. In particular, the sidewall may run perpendicular to the fixing proximal end wall and to the distal end wall.

The opening provided in the first and the third surface may enable an assembly of the bearing to a piston rod body wherein the bearing is moved laterally towards the piston rod body. A lateral movement may correspond to a movement wherein the axis of the bearing is oriented parallel to a longitudinal axis of the piston rod body. In particular, the third surface may define an entry area such that the piston rod body may be assembled to the bearing by moving a part of the piston rod body through that entry area from outside of the bearing into an inner space within the bearing. The entry area may be characterized by a reducing width of the opening provided in the third surface.

This connection of the bearing and the piston rod body is very robust. A reusable drug delivery device may comprise a cartridge which may be removed from the drug delivery device and replaced by a new cartridge when the first cartridge was emptied. During a cartridge change, the bearing may be exposed. Accordingly a regular, axially mounted bearing may be accidentally knocked off or pulled off the piston rod body by a user.

The proposed side loaded bearing provides a very robust assembly and significantly reduces the risk of accidentally knocking off the bearing, as users, in particular untrained users of medical devices, such as patients, during the replacement of the cartridge usually apply axial forces and not radial forces which would be required to remove the bearing from the piston rod body. The proposed bearing will not be disconnected from a piston rod body easily. Further the bearing may be manufactured easily and cheap as a unitary, e.g. moulded, component.

In a preferred embodiment, the third surface defines an entry area wherein the opening provided in the third surface has a minimum width as seen in a cross-section perpendicular to the axis. The third surface may be shaped such that the entry area is confined by two opposing walls. Further, the minimum width may be defined as the smallest distance between the two opposing walls of the third surface in the entry area.

The width of the opening provided in the third surface may reduce in the entry area as seen in a cross-section perpendicular to the axis and in radial direction towards the axis until the minimum width. Thereby, the opening provided in the third surface may form an insertion slant. When the bearing is mounted to a piston rod body, the insertion slant may allow for an assembly if the bearing and the piston rod body are slightly disaligned. In particular, the width of the opening provided in the third surface may reduce in the entry area at an increasing degree towards the minimal width. Thereby, the insertion slant may be convex. A convex insertion slant allows an easier assembly of a piston rod body to the bearing, in particular of a piston rod body comprising curved edges.

Further, the width of the opening provided in the third surface increases as seen in a radial direction towards the axis from the minimum width, thereby the third surface defines a rotational space inside the third surface. The width of the rotational space may be greater than the minimum width. In particular, the rotational space may be cylindrical. Further, the rotational space may be adjacent to the entry area. When the bearing is mounted to a piston rod body, the rotational space may enable the piston rod body to rotate relative to the bearing. In particular, as the width of the rotational space may be greater than the minimum width, a part of the piston rod body may be enabled to rotate inside the rotational space, but prevented from moving out of the rotational space.

Further, the opening provided in the first surface may have a maximum width that is smaller than the width of the opening provided in the third surface at the minimum width, as seen in a cross-section perpendicular to the axis. When the bearing is mounted to a piston rod body, the first surface may prevent an axial movement of the piston rod body relative to the bearing. In particular, a head of the piston rod body having a width bigger than the maximum width of the opening provided in the first surface and further smaller than the minimum width is axially fixed by the opening provided in the first surface.

Flexible elements may be arranged on the third surface. The flexible elements may protrude into the opening. In particular, the flexible elements may protrude into the entry area of the opening. The flexible elements may be shaped such that they allow for an element having a diameter slightly smaller than the minimum width to enter through the entry area in a direction towards the longitudinal axis, but not to exit through the entry area in a direction away from the longitudinal axis.

In a preferred embodiment, the third surface has a C-shaped cross-section as seen in a plane perpendicular to the axis. In another preferred embodiment, the first surface has a C-shaped cross-section as seen in a plane perpendicular to the axis. A C-shaped cross-section presents a simple shape for the first surface and respectively for the third surface wherein an opening is provided realizing the above-mentioned features.

Moreover, according to one aspect a piston rod arrangement is provided comprising a bearing and a piston rod body having a longitudinal axis. The bearing may be mountable to the piston rod body by a movement of the bearing and the piston rod body towards each other with the axis of the bearing and the longitudinal axis of the piston rod body being oriented parallel to each other during said movement. In other words, the bearing may be mounted to the piston rod with a lateral movement.

The piston rod arrangement allows for a very robust assembly of the bearing to the piston rod body. If the bearing is exposed, e.g. during change of a cartridge of a drug delivery device, a user might accidentally knock off or pull the bearing. However, due to the lateral mounting of the bearing to the piston rod body, it is very unlikely that a user accidentally disassembles a piston rod arrangement, once the bearing was assembled to the piston rod body.

In a preferred embodiment of the piston rod arrangement, the piston rod body may comprise a head, wherein the radial width of the head varies along the azimuthal direction around the longitudinal axis. In particular, the head may comprise a minimum radial width. Further, the head may comprise a maximum radial width. A principal direction may be defined as being perpendicular to a direction being defined by the minimum radial width.

In a preferred embodiment, the head may enable an assembly of the bearing to the piston rod body only when the opening provided in the first and the third surface and the principal direction of the head are aligned. Accordingly, the bearing and the piston rod body need to be oriented to each other such that the head may be inserted through the opening provided in the first and the third surface.

As the opening provided in third surface of the bearing may have a width reducing in an entry area, the entry area may comprise an insertion slant. The insertion slant may allow for an assembly of the bearing to the piston rod body even if the openings provided in the first and the third surface and the principal direction of the head are misaligned by a few degrees, e.g. by not more than 20 degrees.

The head may comprise curved edges. Thereby, the curved edges enable the head to slide along the insertion slant of the bearing. Accordingly, the curved edges allow for a smooth interaction of the head with the bearing.

Further, the rotational space of the third surface of the bearing may be wider than the maximum radial width of the head, thereby enabling the head to rotate inside the rotational space.

Moreover, the minimum width of the entry area in the opening provided in the third surface may be equal to or bigger than the minimum radial width of the head and further smaller than the maximum radial width of the head. Thereby, the head is enabled to enter through the entry area defined by the third surface when the principal direction is aligned to the opening. Further, the head is prevented from entering through the entry area defined by the third surface when the principal direction is not aligned to the opening.

In a preferred embodiment, the piston rod body may further comprise a main body part and a connecting portion that connects the head to the main body part. The main body part of the piston rod body may comprise a helical groove. The main body part may be a leadscrew body.

The connecting portion may have a minimum diameter that is smaller than the minimum radial width of the head, as seen in a cross-section perpendicular to the longitudinal axis. However, in a preferred embodiment, the connecting portion has a constant diameter. Accordingly, the minimum diameter of the connecting portion may equal the maximum diameter of the connecting portion.

The maximum width of the opening provided in the first surface may be equal to or bigger than the maximum diameter of the connecting portion and smaller than the minimum radial width of the head. Thereby, the piston rod body is prevented from moving axially relative to the bearing when the bearing is assembled to the piston rod body.

Further, the piston rod body may be enabled to rotate relative to the bearing when the bearing is assembled to the piston rod body. In particular, the head of the piston rod body may be enabled to rotate in the rotational space of the opening provided in the third surface.

According to another aspect of the present disclosure, a drug delivery device comprising a piston rod arrangement is provided wherein the bearing is mounted to the piston rod body.

According to another aspect of the disclosure, a piston rod body is provided, having a longitudinal axis. The piston rod body may comprise a main body part, a head and a connecting portion that connects the head to the main body part, wherein the radial width of the head varies along the azimuthal direction around the longitudinal axis, wherein the head comprises a minimum radial width, and wherein the connecting portion has a diameter that is smaller than the minimum radial width of the head, as seen in a cross-section perpendicular to the longitudinal axis.

Features which are described herein above and below in connection with the bearing and the piston rod body may also be applied for the corresponding drug delivery device and the piston rod arrangement comprising a bearing and a piston rod body.

BRIEF DESCRIPTION OF THE DRAWINGS

Further features, refinements and expediencies become apparent from the following description of the exemplary embodiments in connection with the figures.

DETAILED DESCRIPTION

Like elements, elements of the same kind and identically acting elements may be provided with the same reference numerals in the figures.

The term "medication" or "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 1:
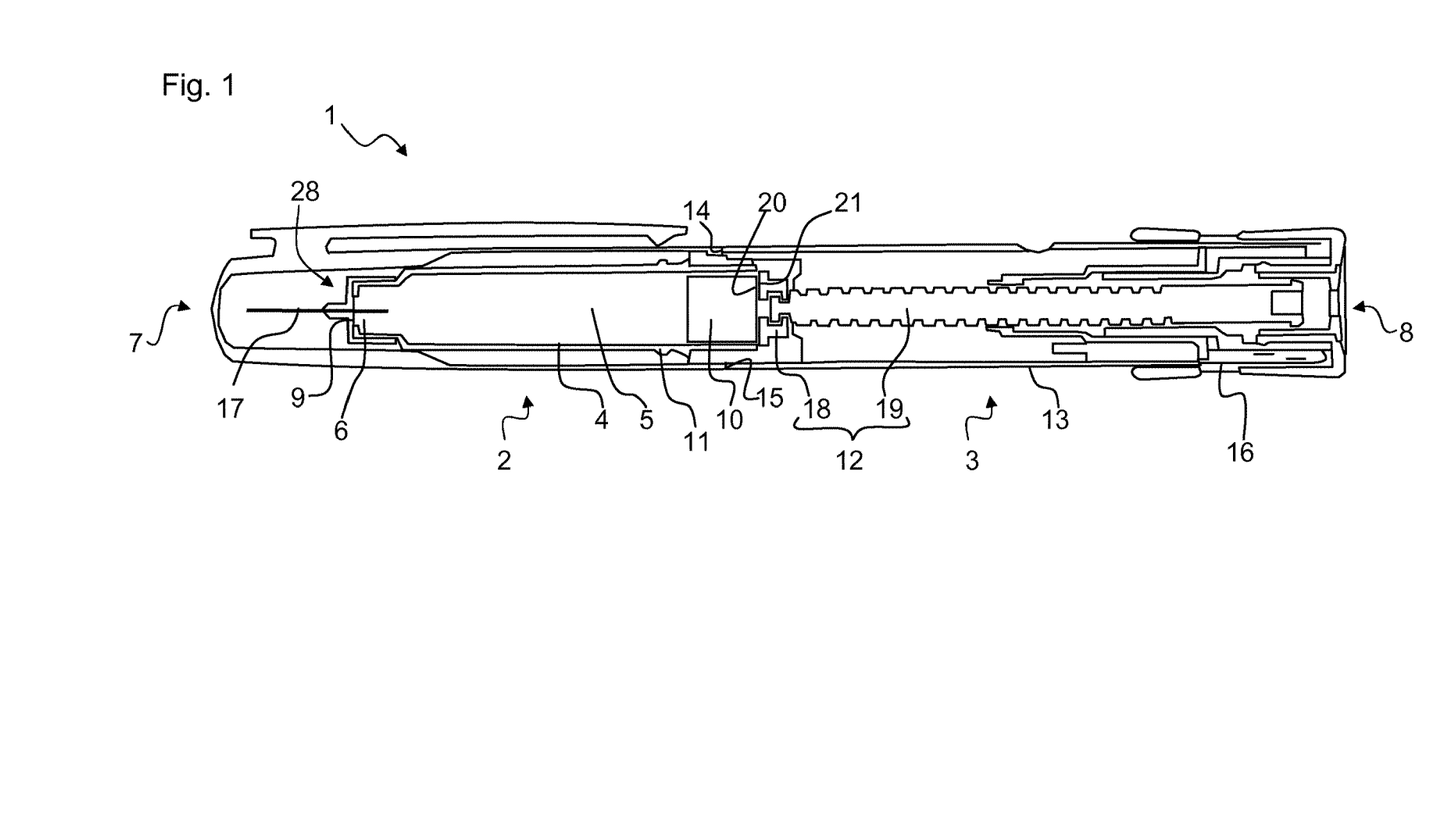
FIG. 1 schematically shows a partial sectional side view of an exemplary embodiment of a drug delivery device.

Turning now to FIG. 1, a drug delivery device 1 is shown which comprises a cartridge unit 2 and a drive mechanism 3. The cartridge unit 2 comprises a cartridge 4. Medication 5 is retained in the cartridge 4. The medication 5 is preferably liquid medication. The cartridge 4 preferably comprises a plurality of doses of the medication 5. The medication 5 may comprise insulin, heparin, or growth hormones, for example. The cartridge 4 has an outlet 6 at its distal end 28. Medication 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

The term "distal end" of the medication delivery device 1 or a component thereof may refer to that end of the device or the component which is closest to the dispensing end of the device 1. The term "proximal end" of the medication delivery device 1 or a component thereof may refer to that end of the device or the component which is furthest away from the dispensing end of the device. In FIG. 1, the distal end of the device 1 is assigned reference numeral 7 and the proximal end of the device is assigned reference numeral 8.

The outlet 6 may be covered by a membrane 9, which protects medication 5 against external influences during storage of the cartridge. For medication delivery, membrane 9 may be opened, e.g. pierced. For example, membrane 9 may be pierced by a needle unit 17. The needle unit 17 may be (releasably) attached to the distal end 7 of the cartridge unit 2. The needle unit 17 may provide for fluid communication from the inside of the cartridge 4 to the outside of the cartridge through outlet 6.

A bung 10 is retained within the cartridge 4. The bung 10 is movable with respect to the cartridge 4. The bung 10 may seal the medication 5 within the cartridge 4. The bung 10 expediently seals the interior of the cartridge 4 proximally. Movement of the bung 10 with respect to the cartridge 4 in the distal direction causes medication 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive mechanism 3.

The cartridge unit 2 and the drive mechanism 3 are secured to one another, preferably releasably secured.

The drive mechanism 3 is configured for transferring force, preferably user-exerted force, particularly preferably manually exerted force, to the bung 10 for displacing the bung 10 with respect to the cartridge 4 in the distal direction. A dose of medication 5 may be dispensed from the cartridge 4 in this way. The size of the delivered dose may be determined by the distance by which the bung 10 is displaced with respect to the cartridge 4 in the distal direction.

The drive mechanism 3 comprises a piston rod arrangement 12. The piston rod arrangement 12 may be configured for transferring force to the bung 10, thereby displacing the piston in the distal direction with respect to the cartridge 4. The piston rod arrangement 12 may comprise a bearing 18 and a piston rod body 19. The bearing 18 may be axially fixed to the piston rod body 19. Thereby, an axial movement of the piston rod body 19 may be converted into an axial movement of the bearing 18.

A distal end face 20 of the bearing may be arranged to abut a proximal end face 21 of the bung 10. The bearing 18 may advance the bung 10.

The drive mechanism 3 comprises a housing 13. The piston rod arrangement 12 may be retained in the housing. A proximal end side 14 of the cartridge unit 2 may be secured to the drive mechanism 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod body" shall preferably mean a component adapted to operate through/within the housing, which may be designed to transfer axial movement through/within the drug delivery device 1, preferably from a drive member to the bung, for example for the purpose of discharging/dispensing an injectable product. Said piston rod body 19 may be flexible or not. It may be a simple rod, a lead-screw, a rack and pinion system, a worm gear system, or the like. "Piston rod body" may further mean a component having a circular or non-circular cross-section. It may be made of any suitable material known by a person skilled in the art and may be of unitary or multipart construction.

The drive mechanism 3 comprises a dose member 16. The dose member 16 is movable with respect to the housing 13. The dose member 16 may be movable in the proximal direction with respect to the housing 13 for setting of a dose of the medication 5 which is to be delivered and in the distal direction with respect to the housing for delivery of the set dose. The dose member 16 is preferably connected to the housing 13. The dose member 16 may be secured against rotational movement with respect to the housing. The dose member 16 may be moved (displaced) between a proximal end position and a distal end position with respect to the housing 13 (not explicitly shown).

The device 1 may be a manually, in particular non-electrically, driven device. The (user-applied) force which causes the dose member 16 to be moved with respect to the housing 13 in the distal direction may be transferred to the piston rod 12 by a drive member. For this purpose, other elements of the drive mechanism may be provided which are not explicitly shown in FIG. 1. The drive mechanism is preferably configured to not move the piston rod 12 with respect to the housing 13 when the dose member 16 is moved in the proximal direction with respect to the housing 13 for setting of the dose.

Embodiments of a drive mechanism which are suitable to be provided in the drug delivery device 1 as it was described above are described in more detail below.

A first embodiment of a drive mechanism which is suitable for being implemented in the medication delivery device 1 as described above is described in connection with FIGS. 2 to 14.

Figure 2:
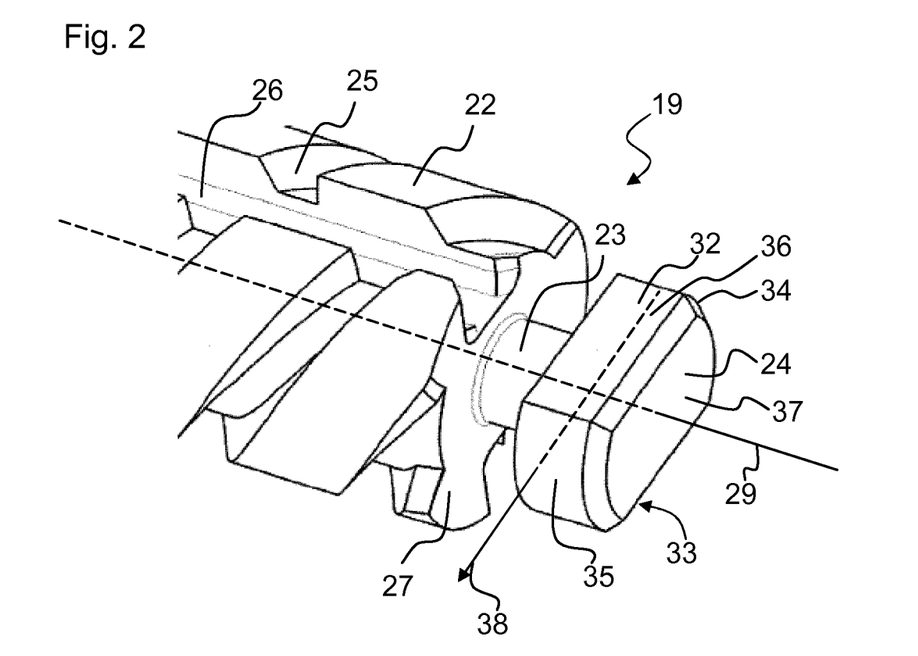
FIG. 2 schematically shows a perspective view of a part of a piston rod body.
Figure 3:
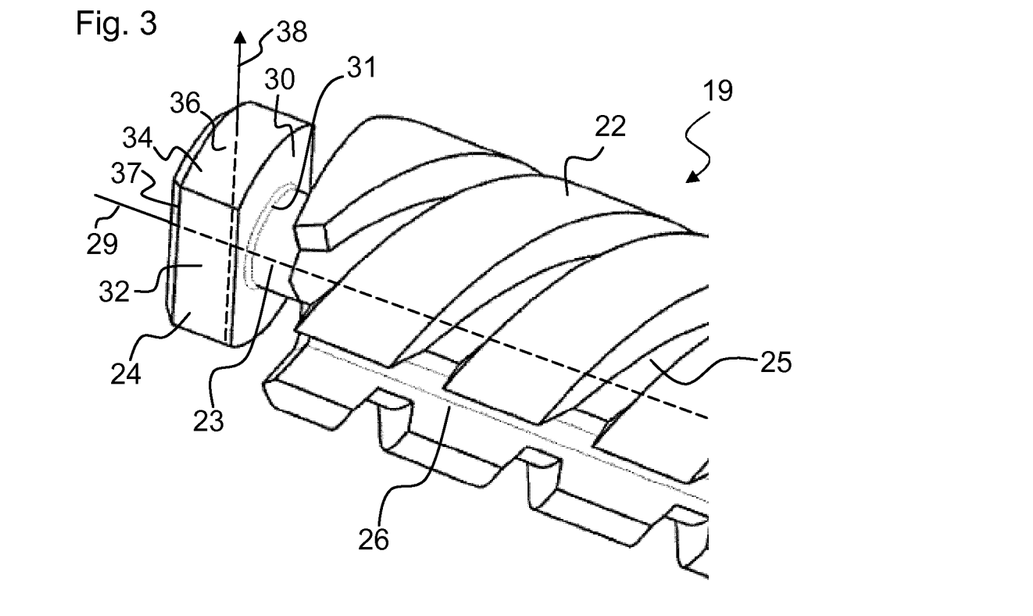
FIG. 3 schematically shows a perspective view of a part of a piston rod body.

FIGS. 2 and 3 show perspective views of a part of the piston rod body 19. The piston rod body 19 has a longitudinal axis 29 and comprises a main body part 22, a connecting portion 23 and a head 24. The piston rod body 19 may be a lead screw. The main body part 22 of the piston rod body comprises a thread 25. The thread 25 of the main body part 22 is helical. An interaction of the thread 25 with parts of a drive mechanism 3 enables the piston rod body to rotate and/or to move axially. Further, the main body part 22 of the piston rod body 19 comprises a linear groove 26 in axial direction. The linear groove 26 allows for interaction with a drive member.

Further, the piston rod body 19 comprises a connecting portion 23, being connected to a proximal end side 27 of the main body part 22. As seen in a cross-section perpendicular to the longitudinal axis 29 of the piston rod body 19, the connecting portion 23 has a circular cross-section. The radial width of the connecting portion 23 is smaller than a minimum radial width of the main body part 22, seen in a cross-section perpendicular to the longitudinal axis 29.

Further, the piston rod body 19 comprises a head 24. The distal end 30 of the head is connected to the proximal end 31 of the connecting portion 23. As seen in a cross-section perpendicular to the longitudinal axis 29, the head 24 comprises four sidewalls 32-35, wherein the first and the second sidewall 32, 33 are opposite to each other and have in radial direction a minimum width. Further, the third and fourth sidewall 34, 35 are also opposite to each other and have in radial direction a maximum width. In longitudinal direction, the head 24 comprises a main section 36 wherein the radial width between the sidewalls 32-35 is constant, and a front section 37 wherein the radial width between the sidewalls 32-35 reduces.

The edges connecting to adjacent sidewalls of the head 24, e.g. the first and the third sidewall 32, 34, are curved.

The first and the second sidewalls 32, 33 have a minimum radial width of the head 24. Thereby, a principal direction 38 of the head 24 is defined being perpendicular to a direction being defined by the minimal width. In this case, the principal direction 38 of the head 24 is defined by being perpendicular to a connecting line of the first and the second sidewall 32, 33.

The minimum radial width of the head 24 is bigger than the diameter of the connecting portion 23. The third and the fourth sidewall 34, 35 have a curved shape.

Figure 4:
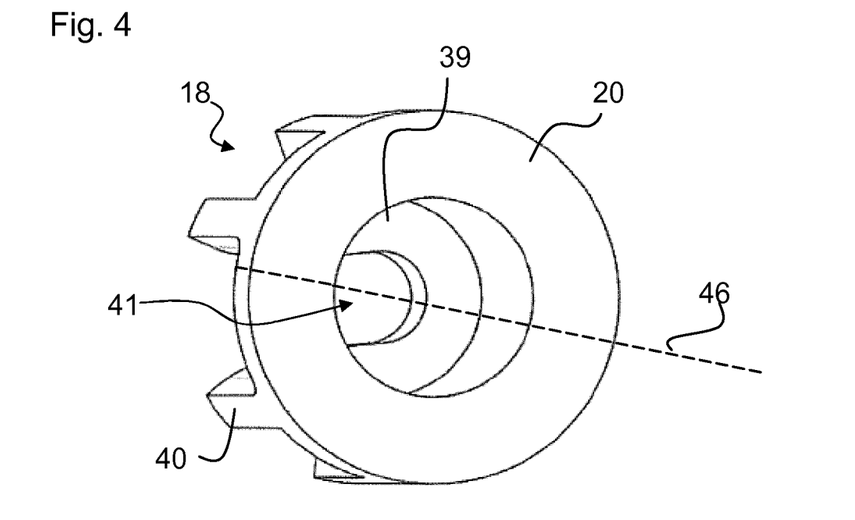
FIG. 4 schematically shows a perspective view of a bearing.
Figure 5:
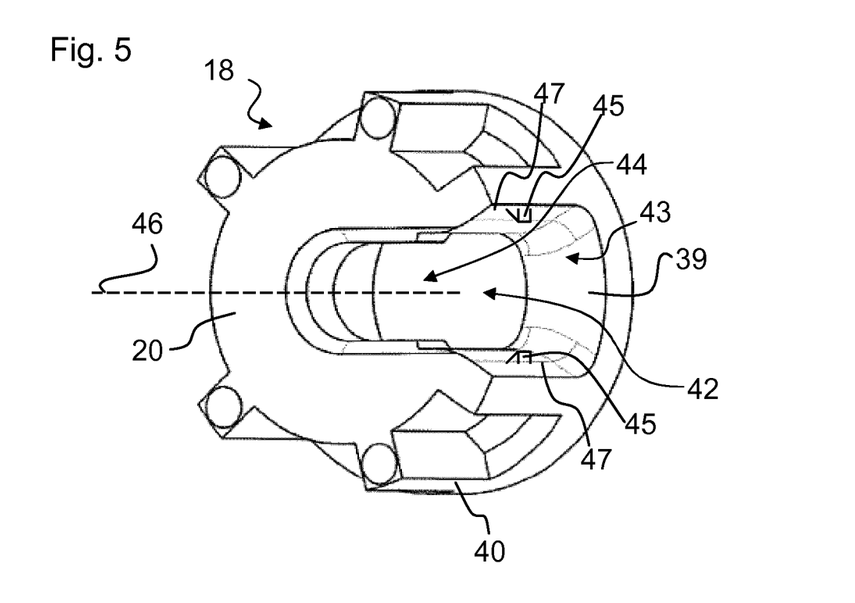
FIG. 5 schematically shows a perspective view of a bearing.

FIGS. 4 and 5 show perspective views of a bearing 18. The bearing 18 comprises a first surface 39, a second surface 20 and third surface 40. The first surface 39 of the bearing 18 may be a fixing proximal end wall. In particular, the fixing proximal end wall may fix the bearing 18 to a piston rod body 19. The second surface 20 of the bearing 18 may be a bung contact wall or a distal end wall 20. In particular, in a drug delivery device 1 the bung contact wall of the bearing 18 may be in direct contact to a bung 10. In particular, the distal end wall 20 of the bearing 18 may be arranged to abut a proximal end face of the bung. The third surface 40 of the bearing 18 may be a sidewall. In particular, the sidewall 40 may be perpendicular to the first surface 39 and to the second surface 20.

The bearing 18 has an axis 46. The first surface 39 and the second surface 20 are spaced apart in the direction of the axis 46. The third surface 40 connects the first and the second surface 39, 20.

As seen in a cross-section perpendicular to the longitudinal axis 29, the first surface 39 has a C-shaped cross-section. An opening 41 is provided in the first surface 39. Seen towards the longitudinal axis 29, the opening 41 has a constant width which is also the maximum width of the opening 41, and in the rear part the width of the opening 41 reduces. The maximum width of the opening 41 provided in the first surface 39 is smaller than the minimum radial width of the head 24 in the main section 36 of the head 24. Further, the maximum width of the opening 41 provided in the first surface 39 is equal to or wider than the diameter of the radial width of the connecting portion 23. Thereby, the opening 41 provided in the first surface 39 allows insertion of the connecting portion 23 of the piston rod body 19 into the first surface 39. However, as the opening 41 provided in the first surface 39 is smaller than the minimum radial width of the head 24, an axial movement of the piston rod body 19 relative to the bearing 18 is prevented.

Seen in a cross-section perpendicular to the longitudinal axis 29, the third surface 40 has a C-shaped cross-section. An opening 42 is provided in the third surface 40. The third surface 40 defines an entry area 43 and a rotational space 44. Seen towards the longitudinal axis 29, the width of the opening 42 provided in the third surface 40 reduces until a minimum width, e.g. until a point of minimum width. The area of reducing width of the opening 42 provided in the third surface 40 is the entry area 43. Further, between the minimum width and the longitudinal axis 29, the width of the opening 42 increases, thereby the third surface 40 defines the rotational space 44 inside the opening 42. In the rotational space 44, the opening 42 provided in the third surface 40 is circular. The diameter of the opening 42 in the rotational space 44 is bigger than the maximum radial width of the head 24. The minimum width is chosen such that this width is equal to or bigger than the minimum radial width of the head 24 and smaller than the maximum radial width of the head 24.

Further, in the entry area 43, protrusions 45 are provided on the sidewall 40. The protrusions 45 may be flexible. The protrusions 45 may be shaped to allow a movement of an element into a direction towards the longitudinal axis 29 and further to restrain a movement away from the longitudinal axis 29.

Figure 6:
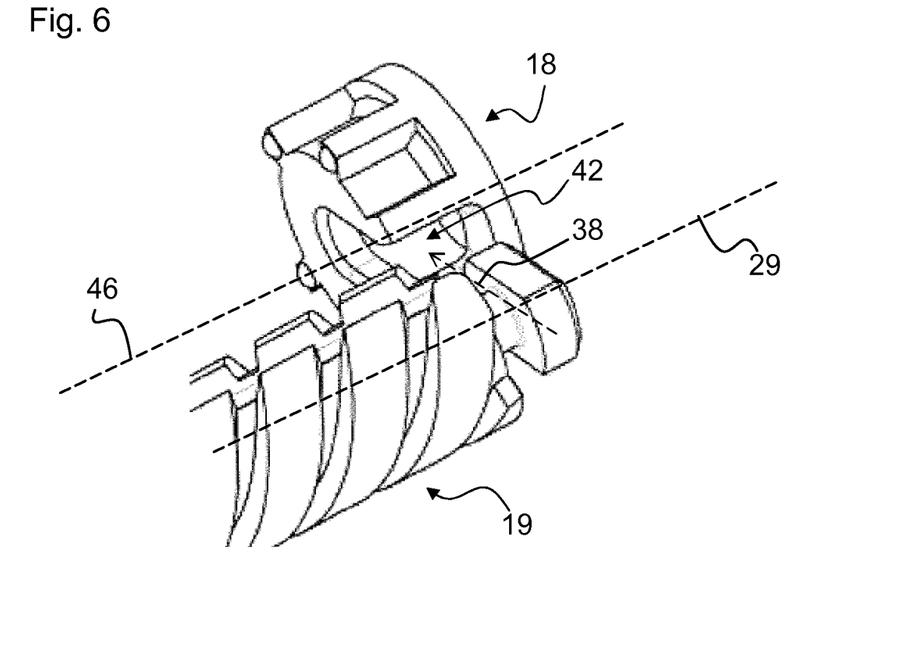
FIG. 6 schematically shows a perspective view of a bearing and a piston rod body in an unassembled state.
Figure 7:
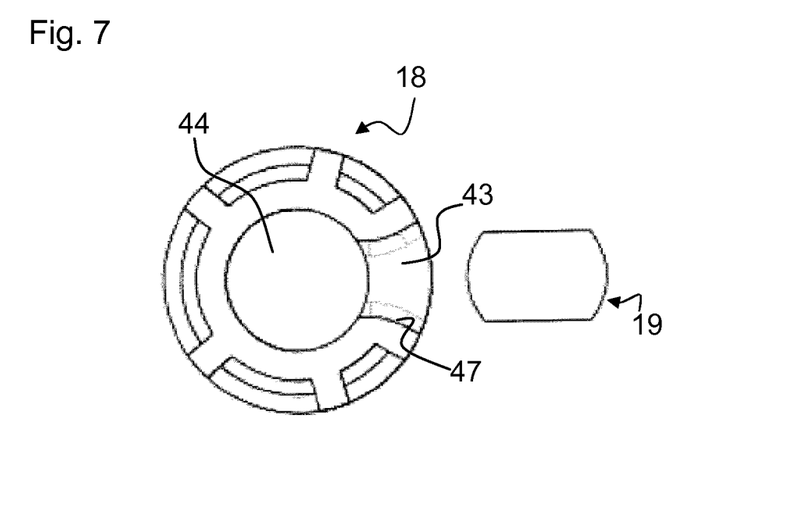
FIG. 7 schematically shows a cross-sectional view of a bearing and a piston rod body in an unassembled state.
Figure 8:
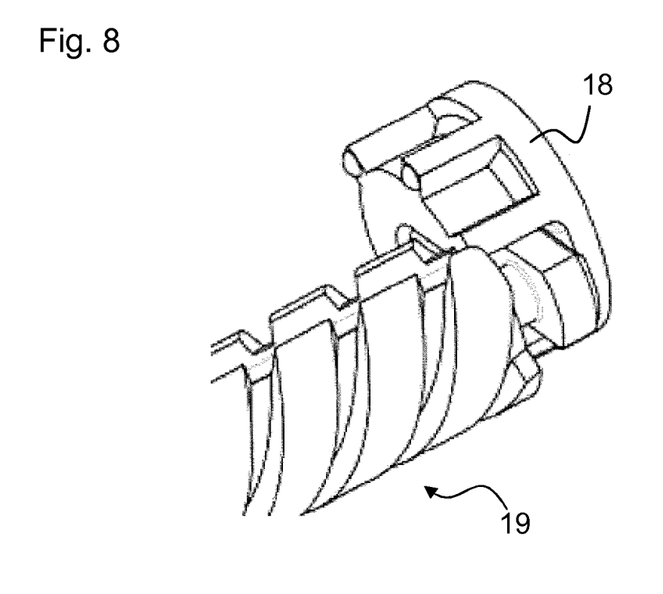
FIG. 8 schematically shows a perspective view of a bearing and a piston rod body during assembly.
Figure 9:
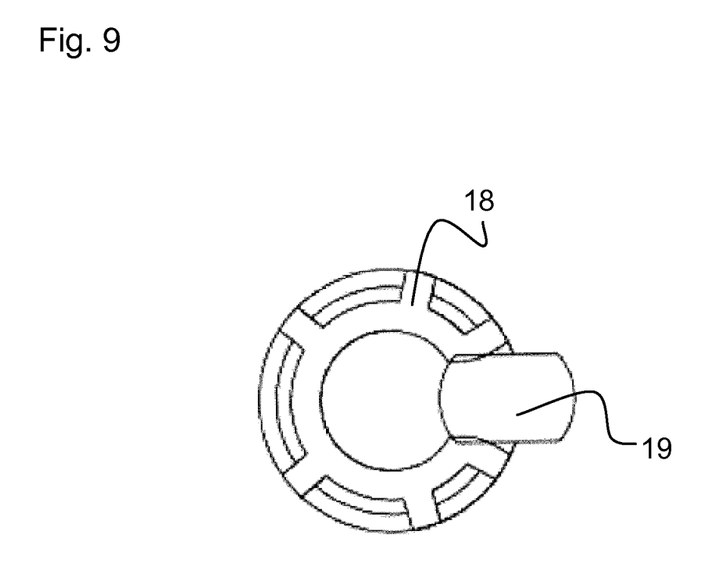
FIG. 9 schematically shows a cross-sectional view of a bearing and a piston rod body during assembly.
Figure 10:
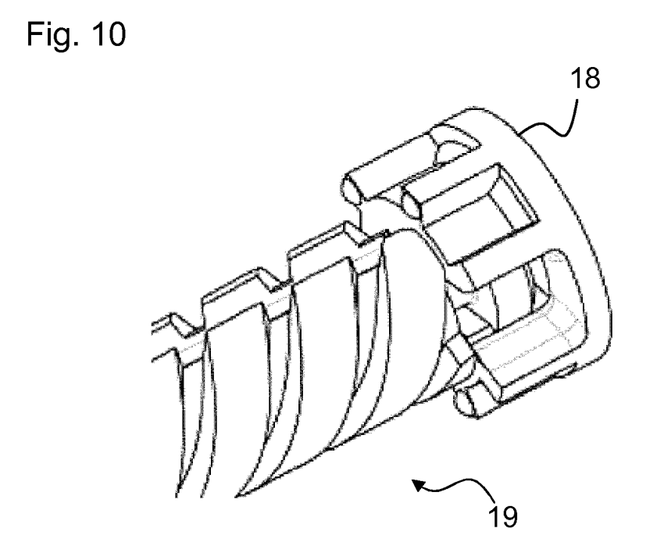
FIG. 10 schematically shows a bearing and a piston rod body in an assembled state.
Figure 11:
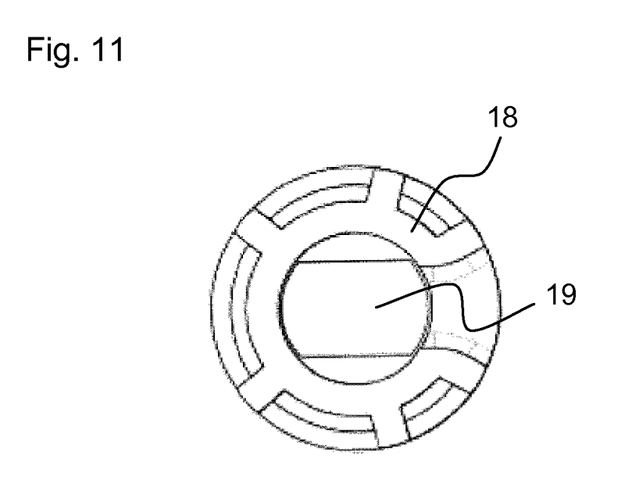
FIG. 11 schematically shows a bearing and a piston rod body in a cross-sectional view in an assembled state.

FIGS. 6-11 show an assembly of the bearing 18 and the piston rod body 19. FIGS. 6, 8, and 10 show the assembly in a perspective view. FIGS. 7, 9, and 11 show the assembly in a cross-section taken perpendicular to the longitudinal axis 29.

FIGS. 6 and 7 show the bearing 18 and the piston rod body 19 in an unassembled state. To mount the bearing 18 to the piston rod body 19, the bearing 18 and the piston rod body 19 are aligned such that the axis 46 of the bearing 18 is perpendicular to the longitudinal axis 29 of the piston rod body 19. Further, they are mounted by a movement wherein the bearing 18 is moved towards the piston rod body 19 and the two axes 46, 29 are kept parallel to each other. In other words, the bearing 18 is mounted to the piston rod body 19 by a lateral movement.

However, the bearing 18 needs to be aligned to the piston rod body 19 to mount it to the piston rod body 19. In particular, a mounting is only possible if the principal direction 38 of the head 24 of the piston rod body 19 is aligned towards the opening 42 provided in the third surface 40 of the bearing 18. As the width of the opening 42 provided in the third surface 40 reduces towards the longitudinal axis 29 until a minimum width, an insertion slant 47 is defined. The insertion slant 47 allows for a manufacturing of the bearing 18 to the piston rod body 19 if they are disaligned by a few degrees, e.g. by not more than 20 degrees. In particular, the width of the opening 42 provided in the third surface 40 reduces towards the longitudinal axis 29 with an increasing degree until a minimum width. Thereby, the insertion slant 47 is shaped convex, allowing for a smooth interaction of the head 24 and the insertion slant 47. The curved edges of the head 24 may slide along the convex surface of the insertion slant 47, thereby enabling an assembly of the head 24 and the bearing 18 even if the axis 46 of the bearing 18 and the longitudinal axis 29 of the piston rod body 19 are slightly misaligned.

FIGS. 8 and 9 show the bearing 18 and the piston rod body 19 during the assembling step.

FIGS. 10 and 11 shows a bearing 18 mounted to the piston rod body 19. The head 24 is positioned in the rotational space 44 of the third surface 40. The head 24 is enabled to rotate relative to the bearing 18 inside the rotational space 44 as the diameter of the opening 42 in the rotational space 44 is bigger than the maximum radial width of the head 24. The protrusions 45 in the entry area 43 of the opening 42 provided in the third surface 40 prevent the head 24 from accidentally moving out of the rotational space 44. The bearing 18 is prevented from an axial movement relative to the piston rod body 19. The maximum width of the opening 41 provided in the first surface 39 being smaller than the minimum radial width of the head 24 prevents the axial movement.

Figure 12:
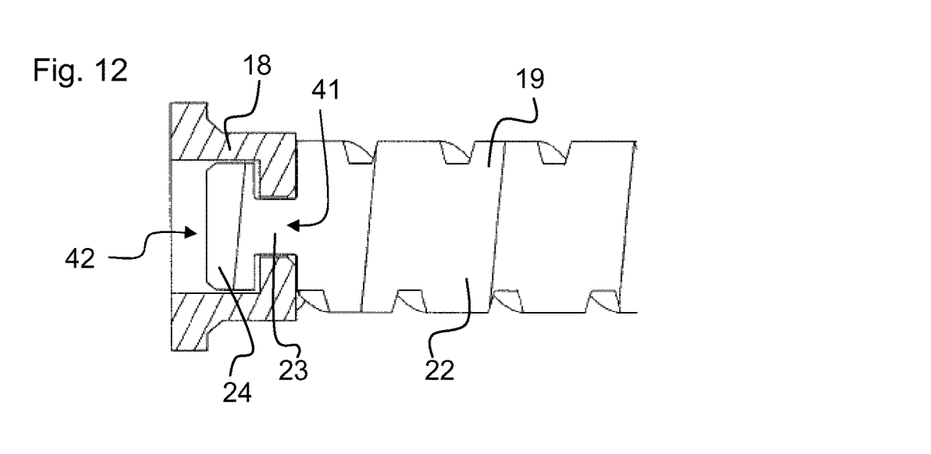
FIG. 12 schematically shows a cross-section of the bearing and the piston rod body in an assembled state taken along the longitudinal axis.

FIG. 12 shows a bearing 18 assembled to a piston rod body 19 in a cross-sectional view taken along the longitudinal axis 29. It can be gathered from FIG. 12 that the maximum width of the opening 41 provided in the first surface 39 being smaller than the minimum radial width of the head 24 prevents the axial movement.

Figure 13A:
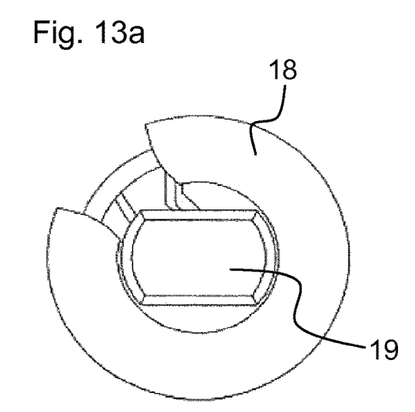
FIG. 13A-13C schematically show cross-sectional views of a bearing and a piston rod body rotated relative to each other in different relative rotation positions.
Figure 13B:
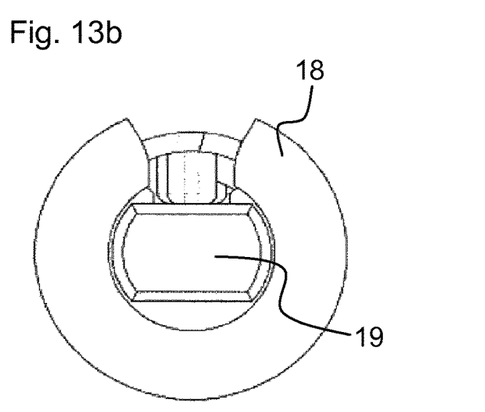
Figure 13C:
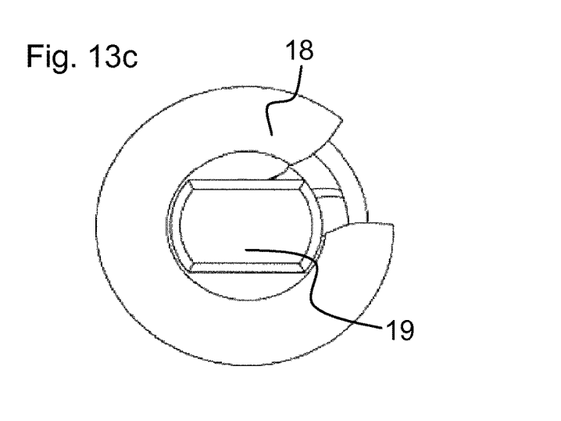

FIGS. 13A-13C show cross-sectional views of the bearing 18 and the piston rod body 19 in a cross-section perpendicular to the longitudinal axis 29. It can be gathered from FIGS. 13A-13C that the head 24 and the piston rod body 19 are enabled to rotate relative to the bearing 18. This is enabled by the rotational space 44 having a width that is wider than the maximum radial width of the head 24.

Figure 14:
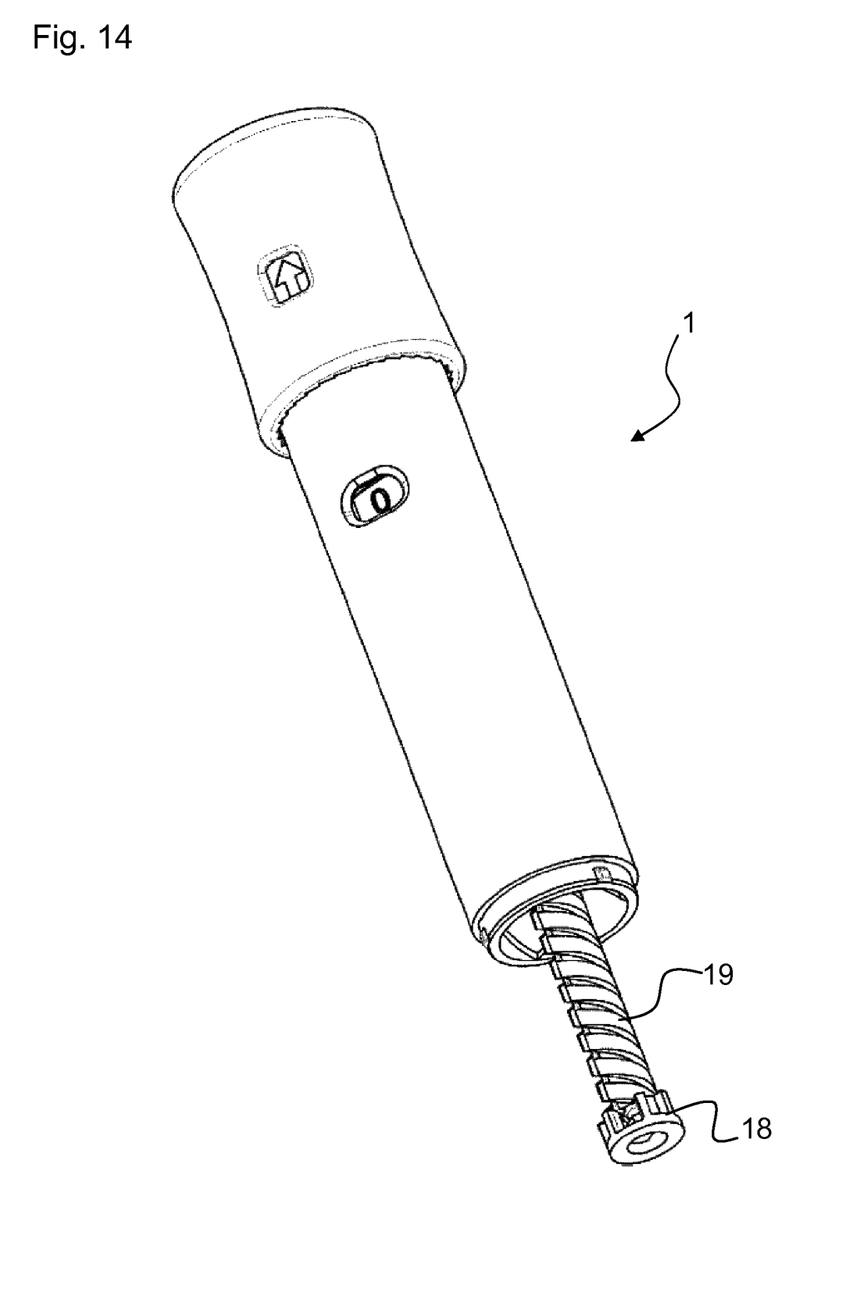
FIG. 14 schematically shows parts of a drug delivery device in a perspective view.

Moreover, FIG. 14 shows parts of a drug delivery device 1 in a perspective view. In particular, a drug delivery device 1 wherein a cartridge holder is removed, e.g. to exchange the cartridge holder, is shown. As the bearing 18 is fixed to the piston rod body 19 in a way that it cannot be knocked off accidentally by a user, the safety and reusability of the device is improved.

The invention claimed is:

1. A drug delivery device comprising:
    a cartridge unit, the cartridge unit comprising a cartridge which contains a drug to be dispensed from the drug delivery device, wherein a bung is retained in the cartridge, wherein the bung seals the interior of the cartridge proximally, and wherein the bung is movable in a distal direction with respect to the cartridge to dispense drug from the cartridge through an outlet of the cartridge; and
    a drive mechanism, wherein
    the cartridge unit is secured to a housing of the drive mechanism, wherein
    the drive mechanism is configured for transferring a force to the bung for displacing the bung with respect to the cartridge in the distal direction, wherein
    the drive mechanism comprises a piston rod arrangement configured for transferring the force to the bung, wherein the piston rod arrangement comprises a bearing and a piston rod body, the bearing being assembled to the piston rod body, wherein
    the bearing has an axis and comprises a first surface and a second surface which are spaced apart in the direction of the axis, the bearing further comprising a third surface, wherein the third surface connects the first surface and the second surface, wherein a first opening is provided in the first surface and a second opening is provided in the third surface, wherein the first opening in the first surface is connected to the second opening in the third surface, and wherein the second surface of the bearing is formed by a bung contact wall which abuts a proximal end face of the bung.

2. The drug delivery device of claim 1, wherein the force transferred by the drive mechanism is manually exerted and user exerted.

3. The drug delivery device of claim 1, wherein the drug delivery device is a pen-type injector.

4. The drug delivery device of claim 1, wherein the drug delivery device is reusable such that the cartridge can be removed from the drug delivery device and be replaced with a new cartridge when the cartridge was emptied, wherein, during a cartridge change, the bearing of the drive mechanism is exposed.

5. The drug delivery device of claim 1, wherein the first opening provided in the first surface has a maximum width that is smaller than the minimum width of the second opening provided in the third surface.

6. The drug delivery device of claim 1, wherein the third surface has a C-shaped cross-section as seen in a plane perpendicular to the axis.

7. The drug delivery device of claim 6, wherein the first surface has a C-shaped cross-section as seen in a plane perpendicular to the axis.

8. The drug delivery device of claim 1, wherein the first surface has a C-shaped cross-section as seen in a plane perpendicular to the axis.

9. The drug delivery device of claim 1, wherein the piston rod body is enabled to rotate relative to the bearing.

10. The drug delivery device of claim 1, wherein the cartridge unit comprises a cartridge retaining member, wherein the cartridge is retained within the cartridge retaining member, and wherein the cartridge retaining member is provided with a fixing member for attaching the cartridge unit to the housing.

11. The drug delivery device of claim 1, wherein the drive mechanism comprises a dose member, the dose member being movable in the proximal direction with respect to the housing for setting of a dose of drug which is to be delivered and in the distal direction with respect to the housing for delivery of the set dose.

12. The drug delivery device of claim 11, wherein the drug delivery device is configured to dispense variable and user-settable doses of the drug.

13. The drug delivery device of claim 1, wherein the piston rod body has a longitudinal axis and comprises a main body part, wherein the main body part of the piston rod body comprises a thread and a linear groove, the linear groove extending in an axial direction along the longitudinal axis and being provided for interaction with a drive member.

14. The drug delivery device of claim 1, wherein the piston rod body has a longitudinal axis and comprises a main body part, a connecting portion and a head, wherein the connecting portion is arranged between the head and the main body part as seen in the axial direction, wherein a radial width of the connecting portion is less than a radial width of the main body part and less than a radial width of the head.

15. The drug delivery device of claim 14, wherein the main body part of the piston rod body comprises a thread and a linear groove, the linear groove extending in an axial direction along the longitudinal axis and being provided for interaction with a drive member.

* * * * *